(12) United States Patent
Yang

(10) Patent No.: US 9,271,865 B2
(45) Date of Patent: Mar. 1, 2016

(54) HOT AND COLD EYE TREATMENT APPARATUS

(71) Applicant: Cheng-Chuan Yang, Taichung (TW)

(72) Inventor: Cheng-Chuan Yang, Taichung (TW)

( * ) Notice: Subject to any disclaimer, the term of this patent is extended or adjusted under 35 U.S.C. 154(b) by 431 days.

(21) Appl. No.: 13/919,988

(22) Filed: Jun. 17, 2013

(65) Prior Publication Data
US 2013/0281893 A1 Oct. 24, 2013

Related U.S. Application Data

(63) Continuation-in-part of application No. 13/044,508, filed on Mar. 9, 2011, now Pat. No. 8,491,505.

(51) Int. Cl.
*A61H 1/00* (2006.01)
*A61F 7/00* (2006.01)
*A61H 23/02* (2006.01)

(52) U.S. Cl.
CPC ........... *A61F 7/0085* (2013.01); *A61H 1/00* (2013.01); *A61H 23/0263* (2013.01); *A61H 2201/0207* (2013.01); *A61H 2201/0214* (2013.01); *A61H 2201/0228* (2013.01); *A61H 2201/0264* (2013.01); *A61H 2201/1607* (2013.01); *A61H 2201/1654* (2013.01); *A61H 2205/024* (2013.01)

(58) Field of Classification Search
CPC ... A61H 23/00; A61H 23/02; A61H 23/0254; A61H 23/0263; A61H 2201/02; A61H 2201/0207; A61H 2201/0214; A61H 2201/0221; A61H 2201/0242; A61H 2201/0257; A61H 2201/0264; A61F 2007/0225; A61F 2007/0228; A61F 7/02; A61F 7/0053; A61F 2007/004; A61F 2007/0054; A61F 2007/0055; A61F 2007/0056; A61F 2007/0071; A61F 2007/0072; A61F 2007/0076; A61F 7/007; A61F 7/0085; A61F 9/00; A61F 9/007; A61F 9/00781; A61F 9/04; A61F 13/124
See application file for complete search history.

(56) References Cited

U.S. PATENT DOCUMENTS

| | | | | |
|---|---|---|---|---|
| 4,574,787 A * | 3/1986 | Jacobs | A61H 39/04 601/148 |
| 4,930,317 A * | 6/1990 | Klein | A61F 7/00 62/259.3 |
| 5,643,336 A * | 7/1997 | Lopez-Claros | A61F 7/02 126/204 |
| 7,355,697 B2 * | 4/2008 | Mertz | G01N 21/0332 356/246 |
| 7,637,878 B2 * | 12/2009 | Lin | A61H 23/0263 601/37 |
| 7,854,754 B2 * | 12/2010 | Ting | A61F 7/10 607/104 |
| 2003/0056281 A1 * | 3/2003 | Hasegawa | A61F 7/02 2/428 |
| 2004/0059400 A1 * | 3/2004 | Lin | A61F 7/007 607/109 |
| 2004/0249427 A1 * | 12/2004 | Nabilsi | A61F 7/0085 607/104 |

\* cited by examiner

*Primary Examiner* — Justine Yu
*Assistant Examiner* — Michael Tsai

(57) ABSTRACT

An eye treatment apparatus includes a hot and cold eye mask and a recirculating water cooling system. The eye mask includes a water pack to be applied onto human eyes, a thermoelectric cooling device for heating or cooling liquid of the water pack, a heat transfer member interposed between the water pack and one side of the thermoelectric cooling device, and a heat exchanger attached to the other side of the thermoelectric cooling device. The thermoelectric cooling device is configured to heat or cool the water pack through the heat transfer member. The water cooling system includes a water supply container and a conduit connecting the water supply container and the heat exchanger to circulate water from the water supply container to the heat exchanger and to return water from the heat exchanger to the water supply container.

12 Claims, 8 Drawing Sheets

HOT AND COLD EYE TREATMENT APPARATUS

CROSS-REFERENCE TO RELATED APPLICATION

This is a continuation-in-part of co-pending application Ser. No. 13/044,508, filed on Mar. 9, 2011.

BACKGROUND OF THE INVENTION

1. Field of the Invention

The present invention relates to an eye treatment apparatus and more particularly to an eye treatment apparatus with a thermoelectric cooling device to apply hot or cold to human eyes.

2. Description of the Related Art

Devices for therapeutic massage of portions of human body are well known, such as evidenced in U.S. Pat. No. 4,574,787. This patent provides an acupressure apparatus for applying vibrational pressure evenly to a plurality of preselected points on a shaped portion of a living body. The apparatus includes a rigid housing and a flexible membrane fixedly secured to said housing so as to form an enclosed chamber between said housing and said flexible membrane for containing a liquid when disposed within, said chamber. Moreover, the apparatus further comprises means for heating said liquid, and therefore the apparatus can simultaneously deliver heat as well as pressure. It is noted that such heating can be accomplished by beating the liquid outside the mask and then supplying the heated liquid to the mask prior to use. This makes it troublesome for the treatment. Alternately, the mask could be filled with the liquid and, and if the mask was constructed of suitable materials, the mask could be placed in a microwave oven for heating. Still another heating means is illustrated in the form of a heater mounted on the mask. The heater is electrically connected to a step down transformer and includes a heating element disposed in the liquid and a thermostat similarly disposed in the liquid. The heater acts in a conventional manner to achieve a preselected temperature for liquid.

While the application of heat is one method for treating the body, it is sometimes necessary that the treatment require the application of cold, rather than heat. It is therefore desirable that the combined massaging and temperature application be tailored to the treatment desired for operating the massaging unit and for the heat or cold.

SUMMARY OF THE INVENTION

It is an objective of the present invention to provide a new hot and cold eye treatment apparatus which utilizes a thermoelectric cooling device to apply hot or cold to human eyes.

Another object in accordance with the present invention is the provision of a hot and cold eye treatment apparatus with a thermoelectric cooling device and a cooling means for heat dissipation of the thermoelectric cooling device.

To achieve the foregoing objectives, the eye treatment apparatus includes a hot and cold eye mask and a recirculating water cooling system. The eye mask includes a water pack to be applied onto human eyes, a thermoelectric cooling device for heating or cooling liquid of the water pack, a heat transfer member interposed between the water pack and one side of the thermoelectric cooling device, and a heat exchanger attached to the other side of the thermoelectric cooling device. The thermoelectric cooling device is configured to heat or cool the water pack through the heat transfer member.

The recirculating water cooling system has a water supply container and a conduit connecting the water supply container and the heat exchanger so as to circulate water from the water supply container to the heat exchanger and to return water from the heat exchanger to the water supply container.

Further benefits and advantages of the present invention will become apparent after a careful reading of the detailed description with appropriate reference to the accompanying drawings.

BRIEF DESCRIPTION OF THE DRAWINGS

In order that the present invention may be more fully understood, it will now be described, by way of example, with reference to the accompanying drawing in which.

DETAILED DESCRIPTION OF EMBODIMENTS

Referring to now to the figures, there is shown an eye treatment apparatus embodying the present invention and generally comprising a hot and cold eye mask 1 (see FIG. 1) and a recirculating water cooling system 2 (see FIG. 5) detachably connected to the eye mask 1.

Figure 1:
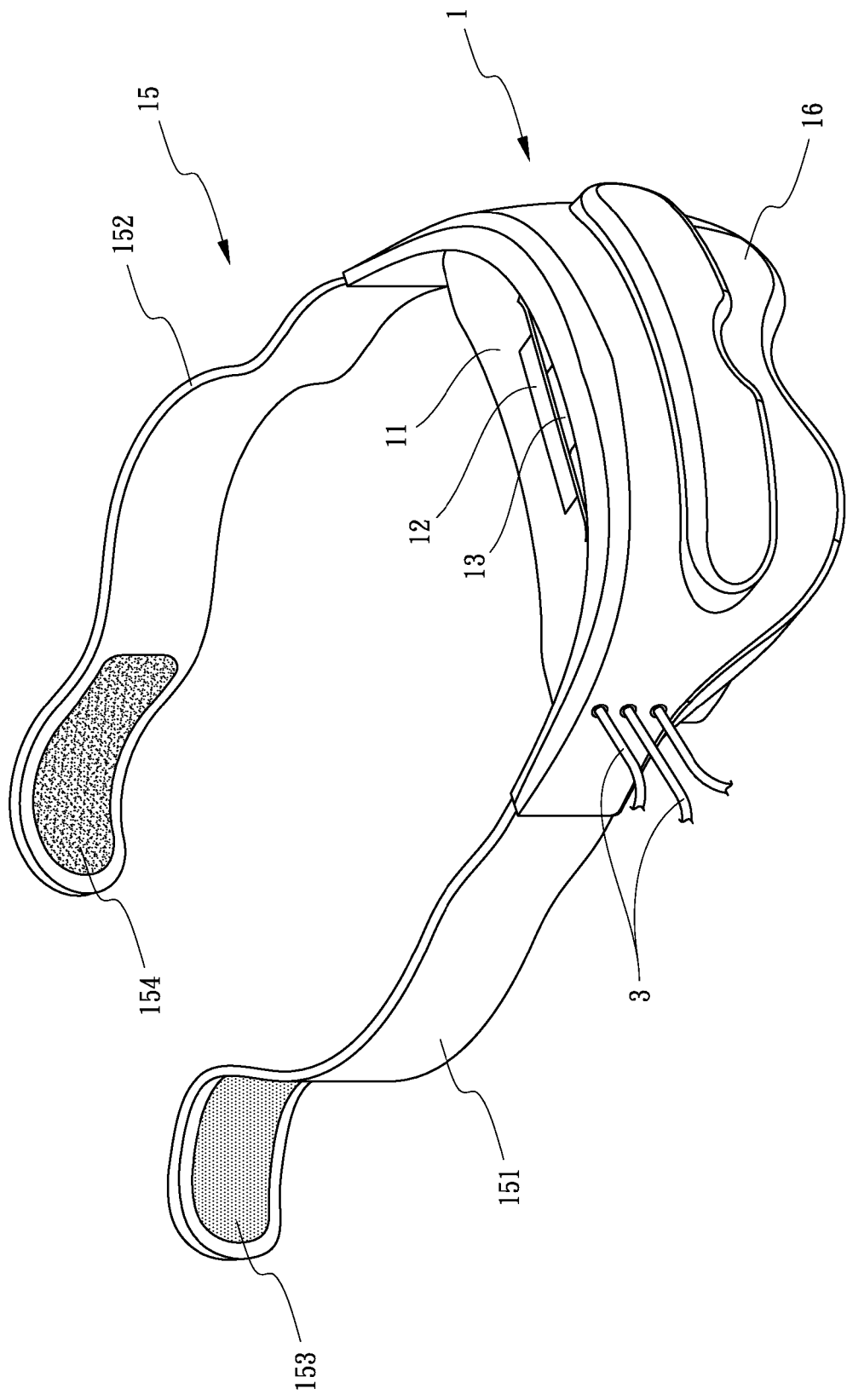
FIG. 1 is a perspective view of a hot and cold eye mask of an eye treatment apparatus in accordance with the preferred embodiment of the present invention.
Figure 2:
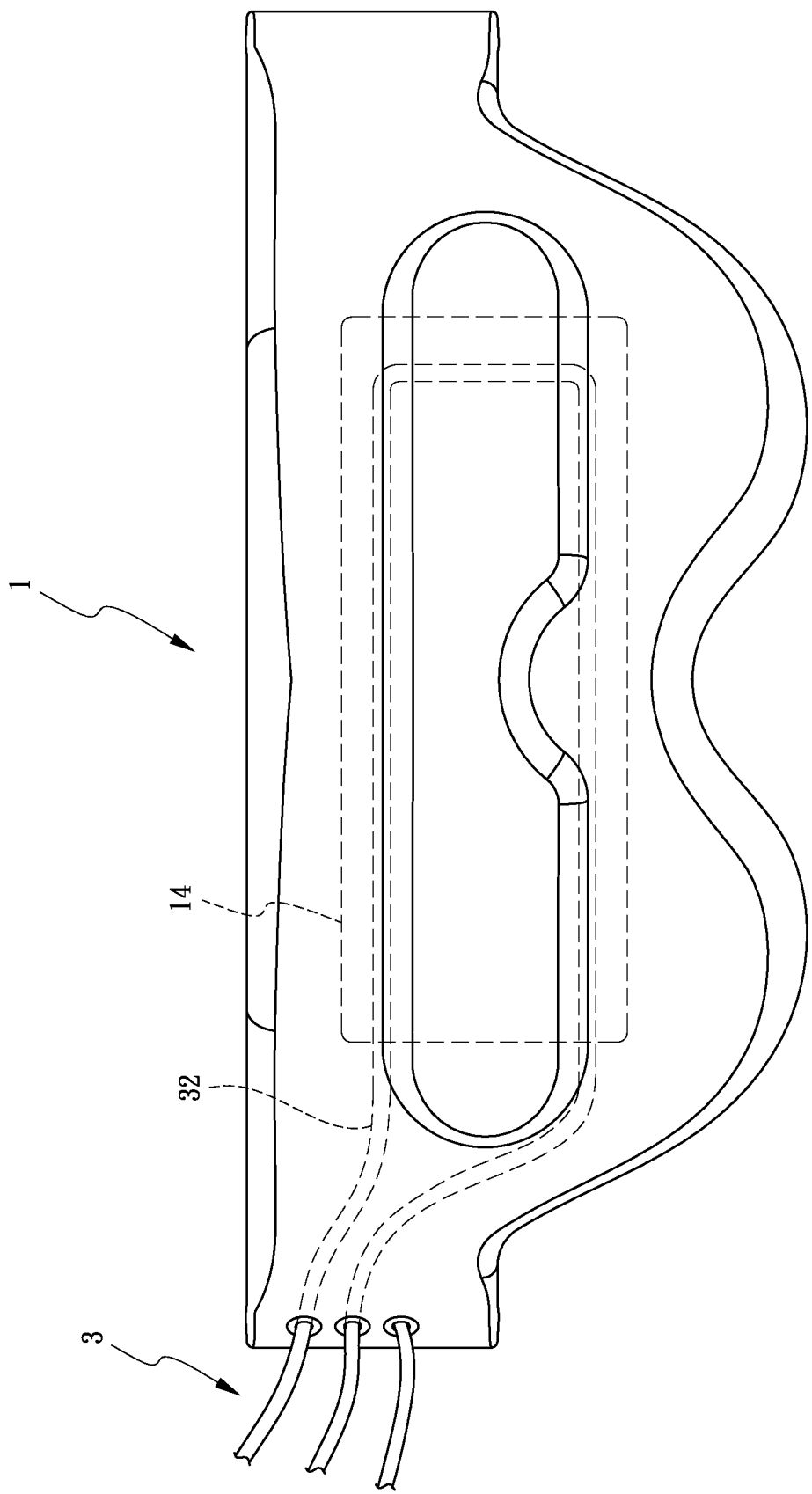
FIG. 2 is a partial front view of the hot and cold eye mask shown in FIG. 1.

As shown in FIGS. 1 and 2, the hot and cold eye mask 1 includes a casing 16, a water pack 11 mounted in the casing 16 to be applied onto human eyes, a semiconductor-based thermoelectric cooling device 13 for heating or cooling liquid of the water pack 11, a heat transfer member 12 interposed between the water pack 11 and one side of the thermoelectric cooling device 13. The thermoelectric cooling device 12 is configured to heat or cool the water pack 11 through the heat transfer member 12 so as to afford some relief to the pain of muscle tension of the eyes. In this embodiment, the water pack 11 has an indentation (see FIG. 4) in which the heat transfer member 12 and the thermoelectric cooling device 13 are embedded.

Moreover, the hot and cold eye mask 1 includes a head strap 15 having a first strap segment 151 and a second strap segment 152 that extend from opposite sides of the casing 16 and are provided with adhesive materials 153, 154 to facilitate mounting and removing the eye mask 1. In this embodiment, the adhesive materials 153, 154 are Velcro material for ease of adjustment and mounting. In other words, the connection between the first and second strap segments 151, 152 is achieved by using a hook and loop connection.

Figure 3:
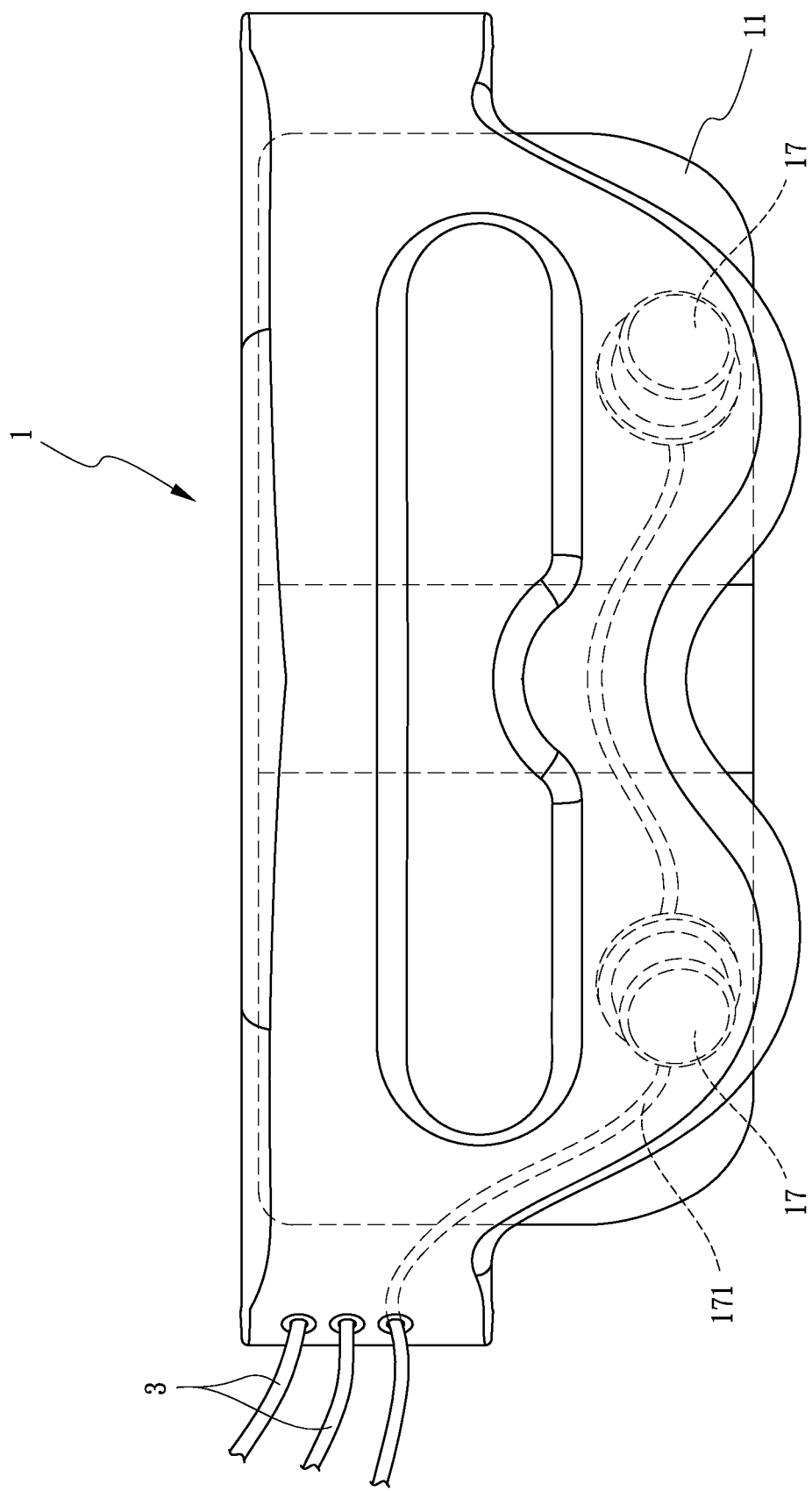
FIG. 3 is another front view of the hot and cold eye mask shown in FIG. 1.

As shown in FIG. 3, the hot and cold eye mask 1 further includes a pair of vibrators 17 disposed on the water pack 11 for providing vibrational energy to the human eyes via the water pack 11. The vibrators 17 is connected to a controller (not shown) via a wire 171. In this manner, the eye treatment apparatus with combined massaging and temperature application is achieved.

Figure 4:
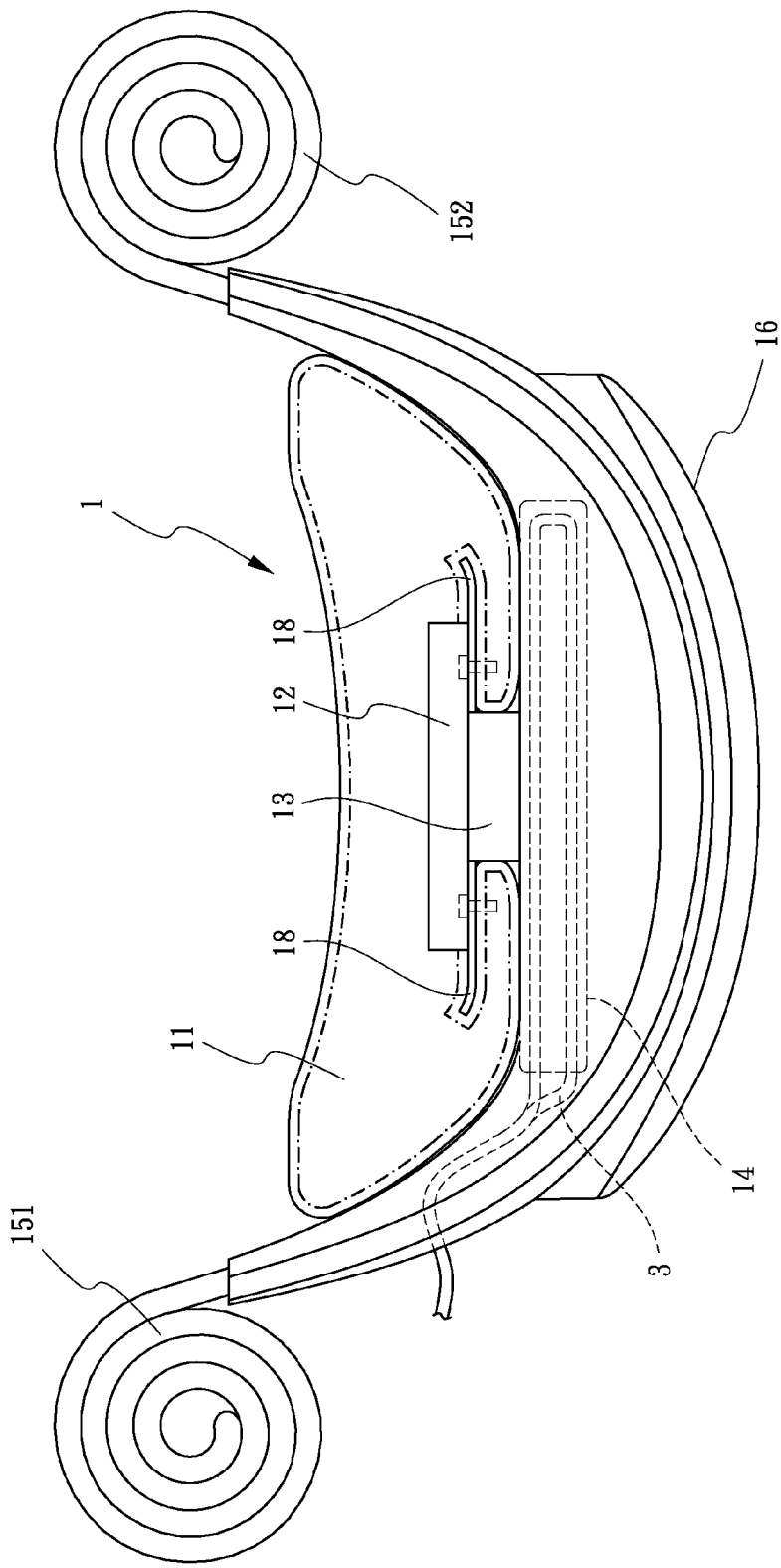
FIG. 4 is a top view of the hot and cold eye mask shown in FIG. 1.

As shown in FIGS. 2 and 4, the hot and cold eye mask 1 further includes a heat exchanger 14 attached to the other side of the thermoelectric cooling device 13. And, the thermoelectric cooling device 13 together with the heat exchanger 14 and the heat transfer member 12 is sandwiched between the casing 16 and the water pack 11. In particular, the hot and cold eye mask 1 may further includes two thermal conductive sheets 18 which is made of Al alloy and extends from opposite sides of the thermoelectric cooling device 13 along surfaces of the heat transfer member 12 to the water pack 11 for enhancing heat transmission between the thermoelectric cooling device 13 and the water pack 11.

Figure 5:
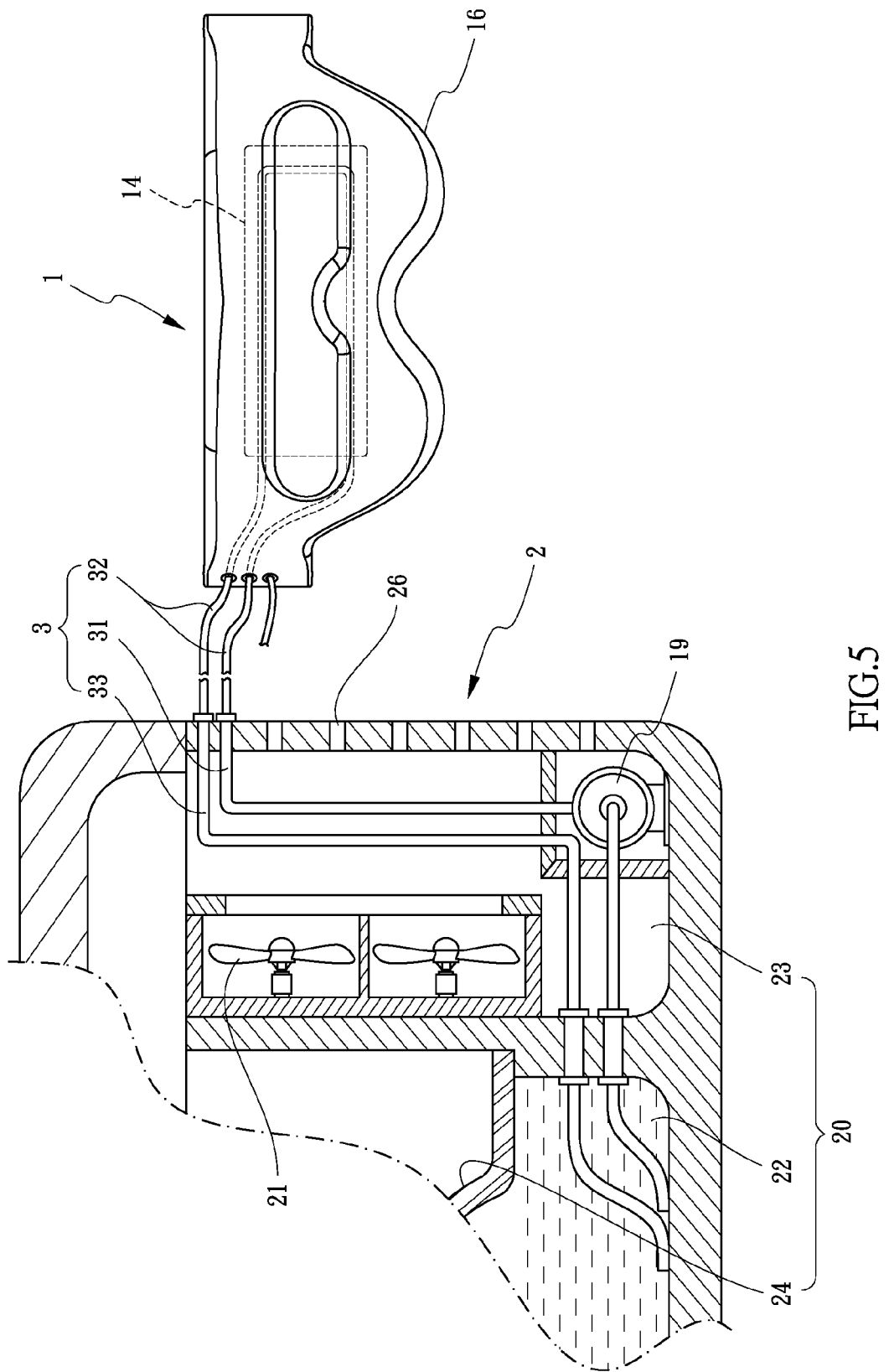
FIG. 5 illustrates a partial cross section of a recirculating water cooling system of the eye treatment apparatus as well as the hot and cold eye mask shown in FIG. 2.

It is to be understood that while in operation, the thermoelectric cooling device 13 may generate a lot of heat needed to be dissipated. Thus, the recirculating water cooling system 2 is provided for cooling the thermoelectric cooling device 13 and therefore maintains the latter function well. As shown in FIG. 5, the recirculating water cooling system 2 has a water supply container 20, a conduit 3 (such as a copper tube) connecting the water supply container 20 and the heat exchanger 14, and a water pump 19 to circulate water from the water supply container 20 to the heat exchanger 14 and to return water from the heat exchanger 14 to the water supply container 20.

Figure 8:
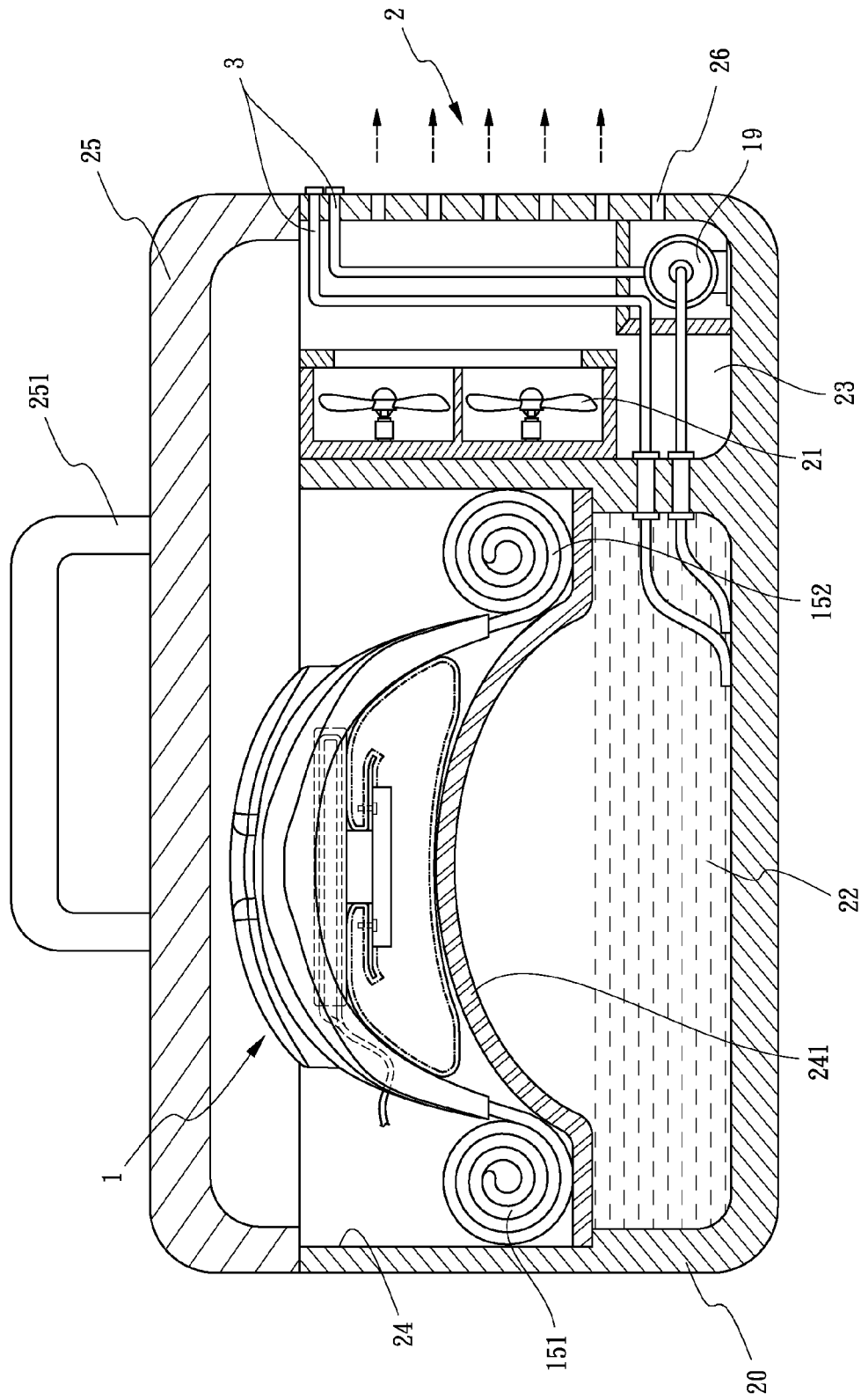
FIG. 8 is a cross section of the eye treatment apparatus, taken along line VIII-VIII of FIG. 7.

Specifically, the water supply container 20 is divided into a water storage room 22, a heat dissipating room 23 next to the water storage room 22, and a mask storage room 24 above the water storage room 22, as best seen in FIG. 8. Referring to FIG. 5, the conduit 3 includes a front pipe section 31, a middle pipe section 32 and a rear pipe section 33. The front and rear pipe sections 31, 33 are disposed in the water supply container 20 while the middle pipe section 32 is disposed outside the water supply container 20. In particular, the middle pipe section 32 has opposite ends detachably connected to the first and third pipe sections 31, 33. Moreover, the front and rear pipe sections 31, 32 extend from the heat dissipating room 23 into the water storage room 22 while the middle pipe section 32 partly extends through the casing 16 into the hot and cold eye mask 1 and wraps around the heat exchanger 14 for cooling the thermoelectric cooling device 13 (FIG. 4). The water pump 19 is disposed in the heat dissipating room 23 and configured to pump water from the water storage room 22 through the front pipe section 31 to the middle pipe section 32 and to return water from the middle pipe section 32 through the rear pipe section 33 back to the water storage room 22.

Referring again to FIG. 5, one or more fan 21 may be included in the heat dissipating room 23 and directed toward the front and rear pipe sections 31, 33 for dissipating heat from the front and rear pipe sections 31, 33. For this, a plurality of vent holes 26 are defined in a wall of the heat dissipating room 23 for air convection, as depicted in FIG. 6, and the front and rear pipe sections 31, 33 may both wind in the heat dissipating room 23 to increase surface area of the same for cooling.

Figure 6:
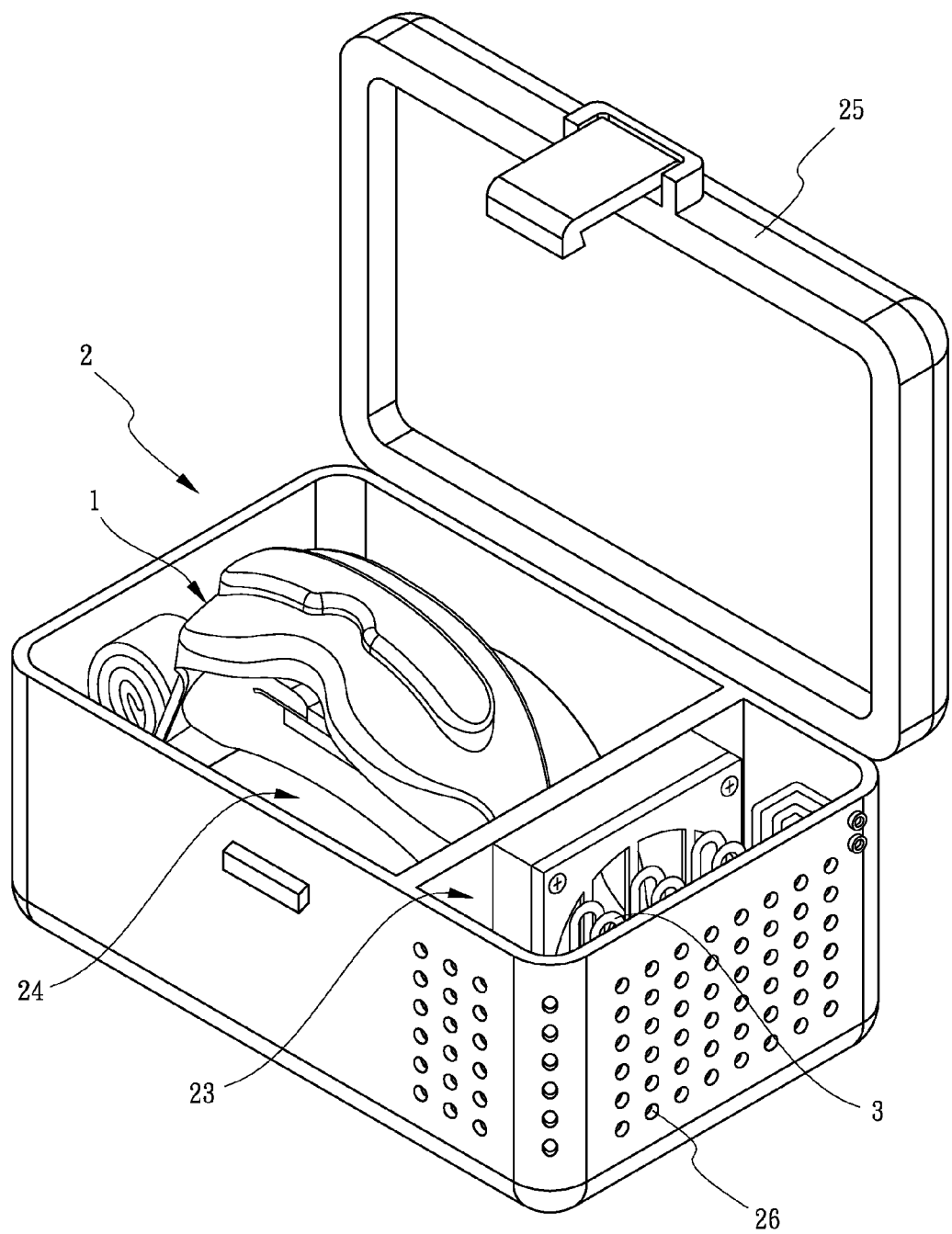
FIG. 6 is a perspective view of the eye treatment apparatus with the cover 25 opened.
Figure 7:
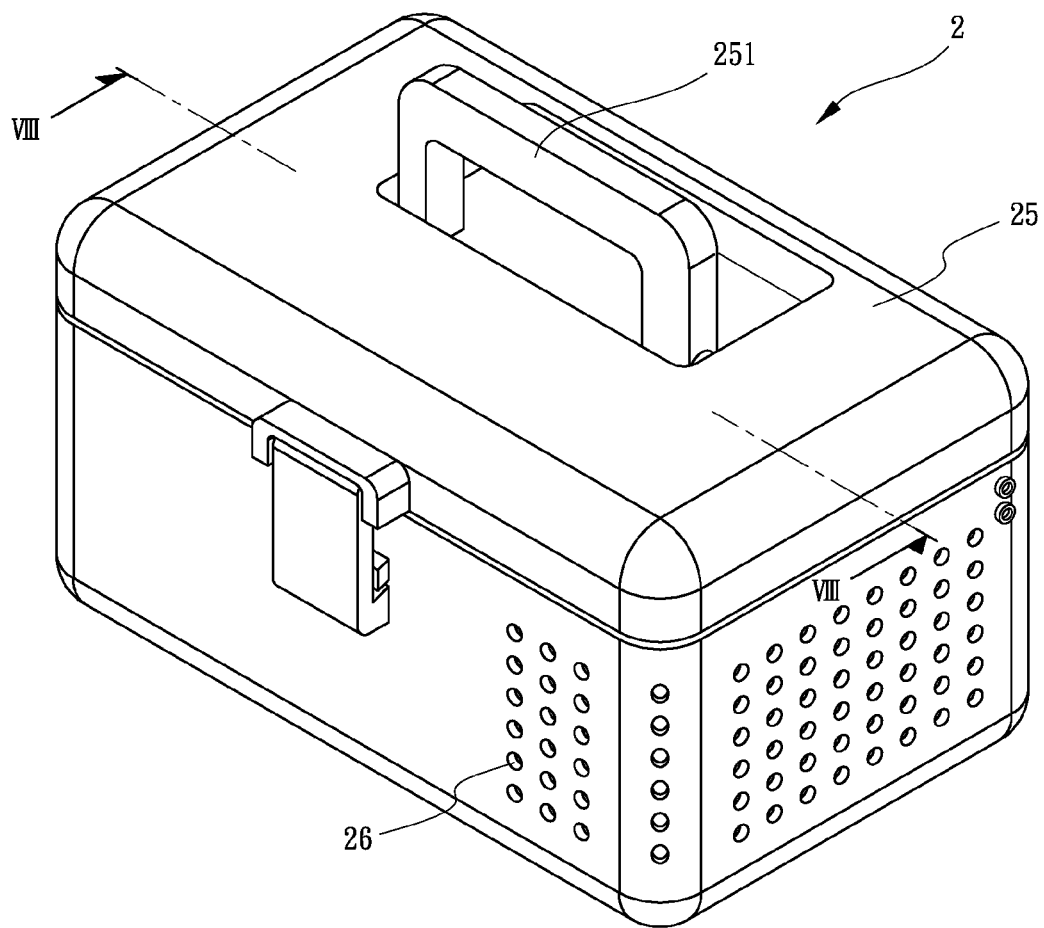
FIG. 7 is another perspective view of the eye treatment apparatus with the cover 25 closed.

Referring to FIG. 6, the mask storage room 24 is configured for storage of the hot and cold eye mask 1 when not in use. In particular, the mask storage room 24 has a convex bottom 241 (FIG. 8) for positioning of the hot and cold eye mask 1. Moreover, for ease of carrying, the water supply container 20 may be formed in a box-like body, as depicted in FIG. 6 or 7, with a cover 25 for covering the mask storage room 24 and the heat dissipating room 23, and a handle 251 mounted on the cover 25.

It is to be understood that the disclosed embodiments are illustrative in nature and the invention is not to be limited to any one or more embodiments except as set forth in the following claims.

What is claimed is:

1. An eye treatment apparatus comprising:
    a hot and cold eye mask including a water pack, a thermoelectric cooling device for heating or cooling liquid of the water pack, a heat transfer member interposed between the water pack and one side of the thermoelectric cooling device, and a heat exchanger attached to the other side of the thermoelectric cooling device; wherein the thermoelectric cooling device is configured to heat or cool the water pack through the heat transfer member; and
    a recirculating water cooling system having a water supply container and a conduit connecting the water supply container and the heat exchanger of the hot and cold eye mask to circulate water from the water supply container to the heat exchanger and to return water from the heat exchanger to the water supply container.

2. The eye treatment apparatus of claim 1, wherein the hot and cold eye mask further includes a pair of vibrators disposed on the water pack for massaging the human eyes.

3. The eye treatment apparatus of claim 1, wherein the hot and cold eye mask further includes a casing in which the water pack is mounted; and the heat exchanger, the heat transfer member and the thermoelectric cooling device are sandwiched between the casing and the water pack.

4. The eye treatment apparatus of claim 3, wherein the hot and cold eye mask further includes a head strap having a first strap segment and a second strap segment that extend from opposite sides of the casing and are detachably connected to each other by a hook and loop connection.

5. The eye treatment apparatus of claim 3, wherein the hot and cold eye mask further includes two thermal conductive sheets extending from opposite sides of the thermoelectric cooling device along surfaces of the heat transfer member to the water pack for enhancing heat transfer between the thermoelectric cooling device and the water pack.

6. The eye treatment apparatus of claim 3, wherein the water supply container of the recirculating water cooling system is at least divided into a water storage room and a heat dissipating room; the conduit includes a front pipe section, a middle pipe section and a rear pipe section, and wherein the front and rear pipe sections are disposed in the water supply container while the middle pipe section is disposed outside the water supply container and has opposite ends detachably connected to the front and rear pipe sections; the front and rear pipe sections extend from the heat dissipating room into the water storage room while the middle pipe section partly extends through the casing into the hot and cold eye mask and wraps around the heat exchanger.

7. The eye treatment apparatus of claim 6, further comprising at least one fan disposed in the heat dissipating room of the water supply container and directed toward the front and rear pipe sections, wherein the water supply container defines a plurality of vent holes in a wall of the heat dissipating room.

8. The eye treatment apparatus of claim 7, wherein the front and rear pipe sections wind in the heat dissipating room.

9. The eye treatment apparatus of claim 7, wherein the recirculating water cooling system further comprises a water pump disposed in the heat dissipating room of the water supply container and configured to pump water from the water storage room through the front pipe section to the middle pipe section and to return water from the middle pipe section through the rear pipe section back to the water storage room.

10. The eye treatment apparatus of claim 6, wherein the water supply container of the recirculating water cooling system further has a mask storage room disposed above the water storage room for reception of the hot and cold eye mask.

11. The eye treatment apparatus of claim 10, wherein the mask storage room has a convex bottom for positioning of the hot and cold eye mask.

12. The eye treatment apparatus of claim 10, wherein the water supply container is formed with a cover for covering the mask storage room and the heat dissipating room, and a handle mounted on the cover.

* * * * *